US00PP19911P2

(12) United States Plant Patent
Sheehan

(10) Patent No.: US PP19,911 P2
(45) Date of Patent: Apr. 14, 2009

(54) GRAPEVINE (SHEEGENE-11)

(50) Latin Name: *Vitis vinifera*
Varietal Denomination: Sheegen-11

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 0 days.

(21) Appl. No.: 12/012,440

(22) Filed: Jan. 31, 2008

(51) Int. Cl.
*A01H 5/00* (2006.01)

(52) U.S. Cl. ..... Plt./207
(58) Field of Classification Search ..... Plt./207
See application file for complete search history.

*Primary Examiner*—Annette H Para
(74) *Attorney, Agent, or Firm*—Baker Manock & Jensen, PC; Eric C. Cole

(57) ABSTRACT

A new and distinct variety of grapevine characterized by the production of large, green-colored seedless grapes that have a muscat flavor and mature in mid to late July, approximately two to three weeks earlier than Thompson Seedless (unpatented) when grown in the San Joaquin Valley of Central California. The grapes of this new variety are produced on strong woody stems and branches and are well adapted to commercial handling.

1 Drawing Sheet

Latin name of the genius and species of the plant claimed:

The claimed plant relates to a new and distinct variety of *Vitis vinifera* to be known as Sheegene-11.

Variety denomination:

This invention relates to a discovery and asexual reproduction of a new variety of *Vitis vinifera*. The new variety of *Vitis vinifera* is the result of hybridization of Princess (unpatented), the pollen parent, and Red Globe (U.S. Plant Pat. No. 4,787), the seed parent. The new variety was first hybridized by Timothy P. Sheehan of Porterville, Calif. in the late Spring 2000. The new variety was asexually propagated in the dormant season of 2003, bud-grafted on Harmony, virus-free rootstock on one vine. The new variety was planted at that time in a *Vitis vinifera* variety block located near Fowler, Calif. on the west side of Thompson Road, north of Adams Road. The new variety produces large, green-colored seedless grapes with a Muscat flavor that mature approximately two to three weeks earlier than Thompson Seedless (unpatented).

BACKGROUND OF THE INVENTION

The present invention relates to a new and distinct variety of grapevine that produces large, green-colored seedless grapes that mature in mid to late July when grown in the San Joaquin Valley of Central California. The new invention resembles Thompson Seedless (unpatented) but the large, green-colored seedless grapes produced by the new variety have a muscat flavor and mature about two to three weeks earlier.

SUMMARY OF THE INVENTION

The Sheegene-11 grapevine is characterized by producing a large, green-colored seedless grape with a muscat flavor that mature for harvesting and shipment in mid to late July when grown in the San Joaquin Valley of Central California. The new variety can be compared to Thompson Seedless (unpatented) but matures approximately two to three weeks earlier, among other distinguishing characteristics.

BRIEF DESCRIPTION OF THE DRAWINGS

The accompanying drawing is a colored photograph of the grapes produced by the new variety; several leaves are displayed as well as a typical section of the vine. The top left of the color photograph displays a secondary growth grape cluster; below is a primary growth grape cluster; and to the right of the primary growth grape cluster is another secondary growth grape cluster. The bottom left of the color photograph is a mature leaf with the stem pointing up and left; the leaf is upside down displaying the bottom surface and petiole. The bottom right of the color photograph displays two new shoot growth tips and tendrils, small leaves with reddish pigment. Above the growth tips are four grapes cut in half longitudinally as well as horizontally displaying the flesh and shape of the fruit. To the right of the grapes that are cut in half is a mature cane displaying nodes, small leaves and one mature leaf which displays the topside with petioles.

DETAILED BOTANICAL DESCRIPTION

Referring more to the horticultural description of the new and distinct variety of grapevine, the following has been observed under the ecological conditions prevailing at the origin vineyard located near Fowler, Calif., in the San Joaquin Valley of Central California. All major color designations are by reference to the Dictionary of Color by Maerz and Paul, First edition, published in 1930. Common color names are also used in several instances.

Vine:

*Size.*—Large for four-year old vine.
*Vigor.*—Very good.
*Chilling requirements.*—Normal for grapevine in the San Joaquin Valley of Central California.
*Figure.*—Wide cordons forming a "T" shaped figure.
*Production capacity.*—Very good.
*Regularity of bearing.*—Regular.

Trunk:

*Size.*—Large: 11 inches [27.94 cm] in circumference, 28 inches [71.12 cm] above graft.

*Surface texture.*—Rough, shaggy.
*Color of dark.*—P1.17 J9 Tanagras Castillian Brown Old Cedar.
*Mature cane color.*—P1.6 F9 Cameo Br.
*Nodes.*—Five nodes on cane, 27–13/16 inches [70.64 cm] in length.
*Length between nodes.*—3–¾ to 6 inches [9.53 to 15.24 cm].
*Lenticel number.*—0.
*Lenticel size.*—0.
*Shoot shape.*—Droopy.
*Tendril number.*—One at node.
*Tendril length.*—1.97 to 3.94 inches [5 to 10 cm].
*Tendril location.*—At nodes.
*Tendril form.*—Bifurcate.
*Tendril texture.*—Firm to slightly woody.
*Bud shape.*—Convex.
*Bud Size.*—1.92 inches [5 mm] in width; 2.76 inches [7 mm] in length.

Branches:
*Size.*—3¼ to 3½ inches [8.26 to 8.89 cm] in circumference.
*Cordons.*—49 inches [124.46 cm] on one side of trunk, 37 inches [93.98 cm] on the other side of trunk.
*Surface texture.*—Slightly rough.
*Color* (*One year or older wood*).—P1.6 G10 Cedar wood Tokay.
*Color* (*immature branches*).—P1.17 L7 Viridine.
*Surface texture* (*immature growth*).—Smooth.
*Lenticel numbers.*—0.
*Lenticels size.*—0.

Leaves:
*Size.*—Large.
*Density.*—Dense.
*Average length.*—5.31 to 6.50 inches [13.5 to 16.5 cm].
*Average width.*—7.56 to 9.25 inches [19.2 to 23.5 cm].
*Shape.*—Pentagonal.
*Texture* (*upper surface*).—Smooth.
*Texture* (*lower surface*).—Glabrous.
*Color* (*upward disposed surface*).—P1.22 L11 Paradise green.
*Color* (*downward disposed surface*).—P1.17 L8 Neva green.
*Color* (*leaf vein*).—P1.17 I6 Viridine green.
*Marginal form.*—Slightly undulate.
*Leaf vein thickness.*—0.079 inches [2 mm].
*Leaf margin.*—Toothed.
*Glandular characteristics.*—0.
*Petiole size.*—Large.
*Petiole length.*—5.79 to 6.77 inches [14.7 to 17.2 cm).
*Petiole thickness.*—0.16 inches [4 mm].
*Petiole color.*—P1.17 I6 Viridine green.
*Petiole sinus form.*—Upside down "U" shape.
*Stem glands form.*—0.
*Stem glands position.*—0.
*Stem glands pattern.*—0.
*Stem glands color.*—0.
*Lobe* (*Average*).—Four.
*Tooth size.*—0.55 inches [14 mm] in length; 0.55 inches [14 mm] in width.
*Tooth number.*—Three to four between lobes.
*Tooth shape.*—Convex.

Fruit:
*Harvesting and shipment.*—Mid to late July in San Joaquin Valley of Central California.
*Solids.*—18.8° Brix.
*Acids.*—0.60.
*Sugar/Acid ratio.*—31.1.
*Juice pH.*—3.54.
*Seeds.*—None
*Capstem pedicel.*—0.28 to 0.35 inches [7 to 9 mm].
*Berry weight.*—8.52 to 9.94 grams.
*Juice color.*—P1.17 I6 Viridine green.
*Cluster size.*—Medium to large.
*Compactness.*—Compact
*Cluster weight.*—1 lb. 8 oz. to 1 lb. 12 oz. (681.6 grams to 795.2 grams].
*Cluster average length* (*without stem*).—0.91 to 0.94 inches [23 to 24 cm].
*Cluster average width.*—0.46 to 0.51 inches [11.8 to 13.0 cm].
*Cluster form.*—Conical.
*Stem.*—Generally variable; 3–¼ inches [8.26 cm].
*Stem caliper.*—0.197 inches (5 mm).
*Berry size.*—Generally large.
*Berry shape.*—Ovate.
*Berry number.*—80 to 158 berries per bunch.
*Berry size* (*average dimension along longitudinal axis*).—3 0.98 inches [25 mm].
*Berry size* (*average dimension along transverse axis*).—0.88 inches [21 mm].

Skin:
*Skin thickness.*—Thin.
*Texture.*—Tough.
*Tendency to crack.*—None known.
*Ground color.*—P1.20 K6 Piguant green.
*Pulp.*—Clear.
*Lenticels.*—None Flesh:
*Flesh color.*—P1.19 L6 Calliste green.
*Juice production.*—Very good.
*Flavor.*—Excellent.
*Aroma.*—Mild.
*Texture.*—Firm.
*Ripening.*—Even.
*Eating quality.*—Very good.
*Use.*—Fresh market.
*Keeping quality.*—Very good.
*Resistance to disease.*—None known.
*Shipping & handling qualities.*—Very good.

Having thus described and illustrated our new variety of grapevine, we claim:

1. A new variety of grapevine to be known as Sheegene-11 and parts thereof, substantially as illustrated and described, characterized principally by its production of large, green-colored seedless grapes that have a muscat flavor and mature approximately two to three weeks earlier in the season of ripening than does Thompson Seedless (unpatented) which it resembles.

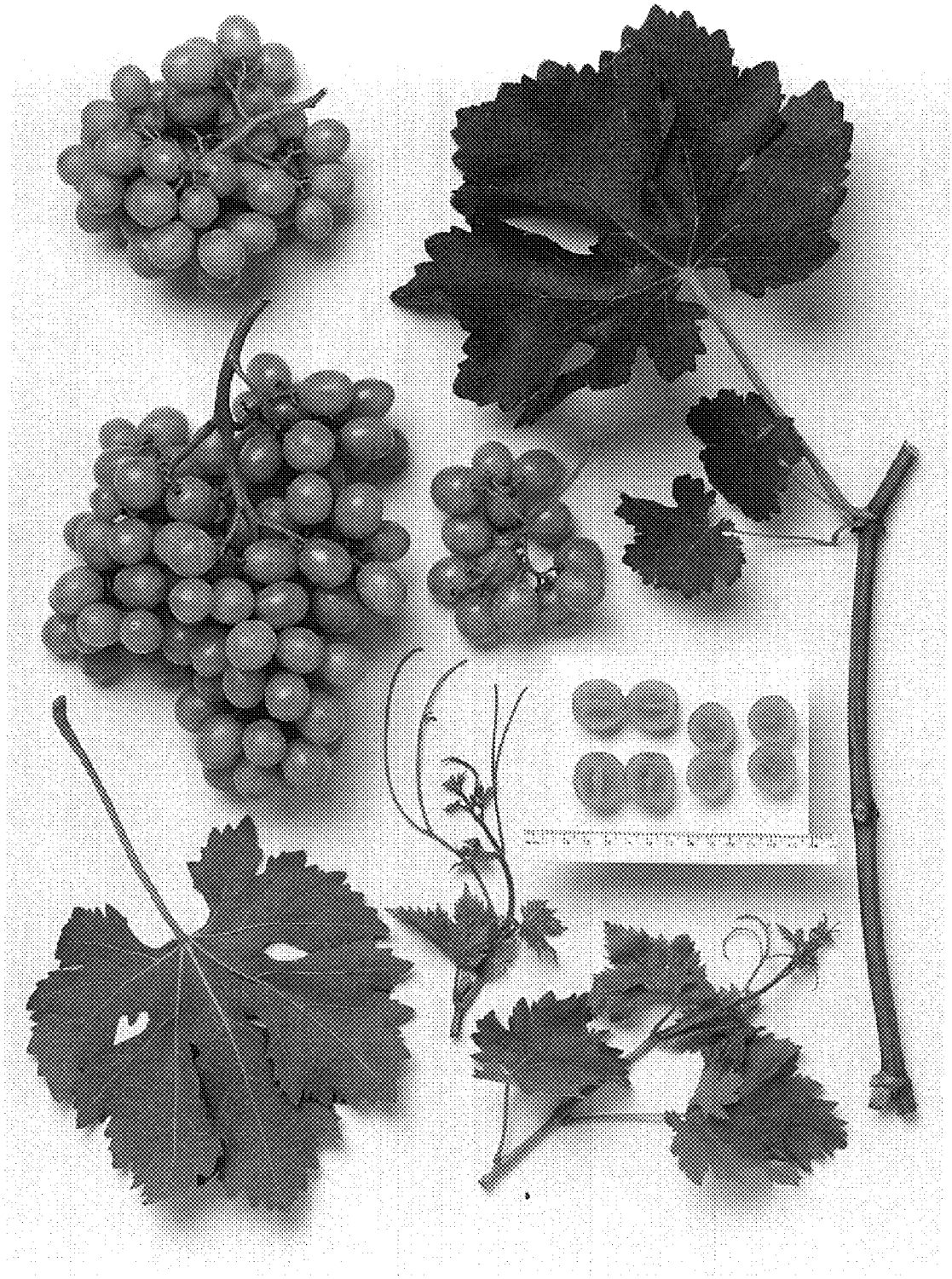

* * * * *